(12) United States Patent
Tatsuta et al.

(10) Patent No.: US 7,935,838 B2
(45) Date of Patent: May 3, 2011

(54) PROCESS FOR PRODUCTION OF STEROID COMPOUND

(75) Inventors: Kuniaki Tatsuta, Tokyo (JP); Kazuo Maruhashi, Saitama (JP); Shingo Yano, Saitama (JP)

(73) Assignee: SRI International, Menlo Park, CA (US)

( * ) Notice: Subject to any disclaimer, the term of this patent is extended or adjusted under 35 U.S.C. 154(b) by 560 days.

(21) Appl. No.: 12/084,037

(22) PCT Filed: Oct. 26, 2006

(86) PCT No.: PCT/JP2006/321330
§ 371 (c)(1),
(2), (4) Date: Apr. 24, 2008

(87) PCT Pub. No.: WO2007/049672
PCT Pub. Date: May 3, 2007

(65) Prior Publication Data
US 2009/0253922 A1  Oct. 8, 2009

(30) Foreign Application Priority Data
Oct. 27, 2005 (JP) .................................. 2005-312853

(51) Int. Cl.
*C07J 1/00* (2006.01)
(52) U.S. Cl. ....................................................... 552/628
(58) Field of Classification Search .................... 552/628
See application file for complete search history.

(56) References Cited

U.S. PATENT DOCUMENTS
6,054,446 A   4/2000  Tanabe et al.
2005/0090477 A1  4/2005  Zorn et al.

FOREIGN PATENT DOCUMENTS
JP   2001-525855 A   12/2001

OTHER PUBLICATIONS

Groh, et al; "Preparation of 3-ketodesogestrel metabolites by microbial transformation and chemical synthesis." Steriods, 1997, vol. 62, No. 5, pp. 437-443.

Rao, et al; "Preparative chemical methods for aromatization of 19-nor-▲4-3-oxosteroids." Steroids, 1994, vol. 59, No. 11, pp. 621 to 627.

*Primary Examiner* — Barbara P Badio
(74) *Attorney, Agent, or Firm* — Kratz, Quintos & Hanson, LLP

(57) ABSTRACT

The present invention relates to a process for production of a steroid compound having a partial structure represented by Formula (2) by oxidizing a steroid compound having a partial structure represented by Formula (1), without the need of any special apparatus, in a safe and economical manner, with less adverse affect on environment, in a simple and high efficient manner. Specifically, the invention relates to a process for producing a steroid compound having a partial structure of ring A and ring B of the steroid skeleton represented by Formula (2):

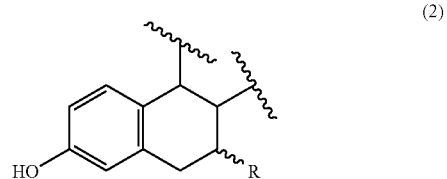

(2)

wherein R represents a hydrogen atom or $C_{1-6}$ alkyl group, comprising the step of reacting a steroid compound having a partial structure of ring A and ring B of the steroid skeleton represented by Formula (1):

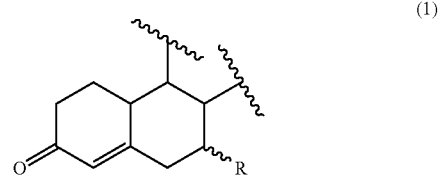

(1)

wherein R is the same as above;
with a catalytic amount of copper halide in the presence of oxygen.

6 Claims, No Drawings

PROCESS FOR PRODUCTION OF STEROID COMPOUND

This application is a 371 of PCT/JP2006/321330 filed Oct. 26, 2006.

TECHNICAL FIELD

The present invention provides a method for producing 7α-methylestrone and derivatives thereof, which are useful as intermediates for medicines, diagnostic agents and the like. The method of the present invention is effective and environmentally friendly.

BACKGROUND OF THE INVENTION

The 7α-methylestrone and derivatives thereof are important compounds as intermediates for manufacturing steroidal anticancer agents and like medicines, and diagnostic agents. Therefore, an effective production process thereof is demanded.

The steroid compound, such as 7α-methylestrone, that has the partial structure of ring A and ring B of its steroid skeleton as shown in Formula (2):

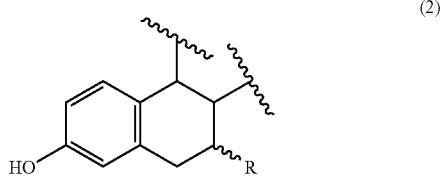

(2)

wherein R represents a hydrogen atom or $C_{1-6}$ alkyl group; is obtained from the steroid compound having the partial structure of ring A and ring B of its steroid skeleton as shown in Formula (1):

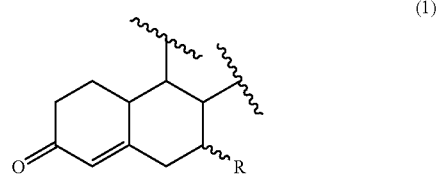

(1)

wherein R is the same as above.

Various methods for producing such steroid compounds in the manner as described above have been reported.

For example, Patent Document 1 discloses in Example 8 that, by using 11β-fluoro-7a-methylestra-4-ene-3,17-dione as a starting material and reacting it with copper (II) bromide in an acetonitrile solvent at 25° C. for 6.5 hours, 11β-fluoro-3-hydroxy-7a-methylestra-1,3,5(10)-triene-17-one can be obtained. However, in this synthetic process, copper (II) bromide is used in an amount of about 2.2 mol per 1 mol of the starting material. Patent Document 1 does not disclose any Synthetic Example wherein a catalytic amount of copper (II) bromide was used.

Non-Patent Document 1 discloses that, in a similar reaction, when copper (II) bromide is used in an amount of less than 1 mol (e.g., 0.9 equivalent) per 1 mol of starting material, the yield of the objective product becomes very low (less than 10%).

Furthermore, Patent Document 2 discloses, in Example 21, a method for producing 7α-methylestrone from 4-estrene-7a-methyl-3,17-dione using copper (II) chloride under an argon atmosphere. However, this is also not an effective method for industrial production in the following respects. In this method, 2 mol of copper (II) chloride is necessary per 1 mol of the starting material. Furthermore, this method requires a long reaction time (72 hours), a troublesome work-up procedure, filtration using expensive silica gel column chromatography for isolation and purification of the objective product, etc. Furthermore, because an excessive amount of copper (II) chloride is necessary in the reaction, i.e., twice that of the starting material in moles, a very large amount of copper waste is generated compared with the amount of the final product, adversely affecting the environment.

As described above, various methods for aromatizing a ring A of a steroid skeleton using a copper halide have been reported. However, a method wherein the ring A is effectively aromatized using only a catalytic amount of copper halide, in particular, a method by which 7α-methylestrone can be produced from 4-estrene-7a-methyl-3,17-dione in an industrially applicable scale and at high yield, has not been reported yet.

Patent Document 1: US Patent Publication No. 2005-90477

Patent Document 2: Japanese Unexamined Patent Publication No. 2001-525855

Non-Patent Document 1: Steroids, 1997, 62, 437-443

DISCLOSURE OF THE INVENTION

Problem to be Solved by the Invention

An object of the present invention is to provide a process for easily and effectively producing a steroid compound having a partial structure represented by Formula (2) by oxidizing a steroid compound having a partial structure represented by Formula (1). The method of the present invention does not require any special apparatus, is highly safe, very economical, and more environmentally friendly than prior art techniques. Specifically, the present invention provides a method for producing 7α-methylestrone from 4-estrene-7a-methyl-3,17-dione at a high yield, even on a mass-production scale.

Means for Solving the Problem

The present inventors conducted intensive research to solve the above-mentioned problems and found that, by reacting a steroid compound having the partial structure of ring A and ring B of its steroid skeleton represented by Formula (1)(specifically, 4-estrene-7a-methyl-3,17-dione) with a catalytic amount of copper (II) bromide or copper (II) chloride in the presence of oxygen, the oxidation reaction can be effectively promoted, so that a steroid compound having the partial structure of ring A and ring B of its steroid skeleton represented by Formula (2)(specifically, 7α-methylestrone) can be obtained. The present inventors conducted further research and have accomplished the present invention based on these findings.

In other words, the present invention provides the processes for production of a steroid compound as below.

Item 1. A process for producing a steroid compound having a partial structure of ring A and ring B of a steroid skeleton represented by Formula (2):

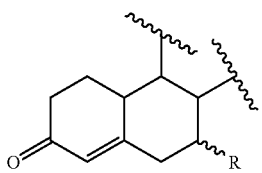

(2)

wherein R represents a hydrogen atom or $C_{1-6}$ alkyl group, comprising the step of reacting a steroid compound having a partial structure of ring A and ring B of a steroid skeleton represented by Formula (1):

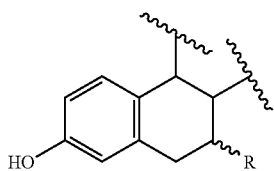

(1)

wherein R is the same as above;

with a catalytic amount of copper halide in the presence of oxygen.

Item 2. A production process according to Item 1, wherein 0.05 to 0.95 mol of copper halide is used per 1 mol of a steroid compound having the partial structure of ring A and ring B of the steroid skeleton represented by Formula (1).

Item 3. A production process according to Item 1 or 2, wherein the copper halide is copper (II) bromide or copper (II) chloride.

Item 4. A production process according to any one of Items 1 to 3, wherein the reaction is conducted while supplying an oxygen-containing gas to a mixture of a steroid compound having the partial structure of ring A and ring B of the steroid skeleton represented by Formula (1), a catalytic amount of copper halide, and a solvent.

Item 5. A production process according to any one of Items 1 to 4, wherein R in Formula (1) and Formula (2) is methyl group.

Item 6. A production process according to any one of Items 1 to 5, wherein the steroid compound having the partial structure of ring A and ring B of the steroid skeleton represented by Formula (1) is 4-estrene-7a-methyl-3,17-dione and the steroid compound having the partial structure of ring A and ring B of the steroid skeleton represented by Formula (2) is 7α-methylestrone.

The present invention is explained in detail below.

Examples of $C_{1-6}$ alkyl groups represented by R in Formula (1) of the partial structure of ring A and ring B of the steroid skeleton are straight or branched alkyl groups, including methyl, ethyl, propyl, isopropyl, n-butyl, isobutyl, tert-butyl, n-hexyl and the like. Among these, methyl is preferable.

The stereochemistry of R in the ring B may be either a- or β-configuration, but a-configuration is preferable.

A steroid compound having a partial structure of ring A and ring B of the steroid skeleton represented by Formula (1) can be shown by Formula (3):

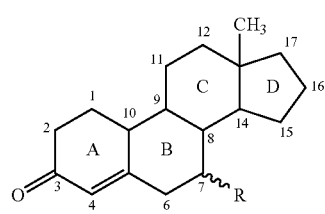

(3)

wherein R is the same as above.

The steroid compound may have a substituent in its C ring and D ring, and the types and positions of the substituent/substituents are not limited as far as they do not adversely affect the reaction of the present invention.

Examples of substitution positions that do not adversely affect the reaction of the present invention include 11-position, 12-position, 15-position, 16-position, 17-position, etc.

Examples of the substituents that do not adversely affect the reaction of the present invention include halogen atoms (fluorine, chlorine, bromine, and iodine), hydroxyl group, oxo group, $C_{2-7}$ acyloxy group, $C_{1-10}$ alkyl group that may have a substituent, $C_{1-7}$ acyl group that may have a substituent, $C_{7-11}$ aralkyl group that may have a substituent, $C_{2-4}$ alkenyl group, $C_{2-4}$ alkynyl group, $C_{1-4}$ alkylidene group that may have a substituent, and the like.

Examples of $C_{2-7}$ acyloxy groups include acetyloxy group, propionyloxy group, butyryloxy group, isobutyryloxy group, isovaleryloxy group, pivaloyloxy group, heptanoyloxy group and the like.

Examples of $C_{1-10}$ alkyl groups include methyl, ethyl, propyl, isopropyl, butyl, isobutyl, tert-butyl, pentyl, isopentyl, hexyl, heptyl, octyl, nonyl, decyl and the like. These alkyl groups may have a substituent, and the examples of the usable substituents include halogen atoms, hydroxyl group, hydroxy carbonyl group, $C_{1-4}$ alkoxy groups (methoxy, ethoxy, propoxy, isopropoxy, butoxy, isobutoxy and the like), $C_{1-5}$ acyl groups (formyl, acetyl, propionyl, butyryl, isobutyryl, isovaleryl, pivaloyl and the like), and $C_{6-10}$ aryloxy groups (phenoxy, naphthyloxy and the like) that may have one to three substituents.

Examples of substituents in the $C_{6-10}$ aryloxy groups that may have one to three substituents include halogen atoms, hydroxyl group, $C_{1-4}$ alkyl groups (methyl, ethyl, propyl, isopropyl, butyl, isobutyl, t-butyl and the like), $C_{1-4}$ alkoxy groups (methoxy, ethoxy, propoxy, isopropoxy, butoxy and the like), $C_{2-6}$ dialkylamino groups (dimethylamino, diethylamino, dipropylamino, diisopropylamino and the like), $C_{1-4}$ acyl groups (formyl, acetyl, propionyl, butyryl and the like), $C_{2-6}$ alkoxy alkyl groups (methoxy methyl, methoxy ethyl, methoxy propyl, ethoxy ethyl, isopropoxy ethyl, ethoxybutyl and the like), $C_{3-9}$ dialkylamino carbonyl groups (dimethylamino carbonyl, diethylamino carbonyl, dipropylamino carbonyl, dibutylamino carbonyl and the like), $C_{3-9}$ dialkylamino alkyl groups (dimethylaminomethyl, dimethylaminoethyl, dimethylaminopropyl, diethylaminomethyl, diethylaminoethyl, diethylaminopropyl, diisopropylaminomethyl, dibutylaminomethyl and the like), etc.

Specific examples of $C_{1-7}$ acyl groups include formyl, acetyl, propionyl, butyryl, isobutyryl, isovaleryl, pivaloyl, heptanoyl and the like. These acyl groups may have substituents those exemplified in the explanation of the alkyl group that may have a substituent.

Specific examples of $C_{7-11}$ aralkyl groups include benzyl, phenethyl, phenylpropyl, naphthylmethyl and the like. These aralkyl groups may have substituents those exemplified in the explanation of the alkyl group that may have a substituent.

Specific examples of $C_{2-4}$ alkenyl groups include vinyl, allyl, isopropenyl, 2-butenyl and the like.

Specific examples of $C_{2-4}$ alkynyl groups include ethynyl, 2-propynyl, 2-butynyl and the like.

Specific examples of $C_{1-4}$ alkylidene groups include methylidene, ethylidene, propylidene and the like. Examples of substituents that may be included in these alkylidene groups are the same as those included in the above-described alkyl groups, and $C_{2-7}$ alkoxycarbonyl groups (for example, methoxycarbonyl, ethoxycarbonyl, propoxycarbonyl, butoxycarbonyl and the like).

A preferable example of the steroid compound, which is used as the starting materials, having the partial structure of ring A and ring B of the steroid skeleton represented by Formula (1) is 4-estrene-7a-methyl-3,17-dione. A preferable example of the steroid compound having the partial structure of ring A and ring B of the steroid skeleton represented by Formula (2) is 7α-methylestrone, which is obtained from the above-mentioned starting material steroid compound. The starting material, 4-estrene-7a-3,17-dione, is commercially available, for example, from Steraloids, Inc., etc.

The production process of the present invention can be expressed by the reaction steps as below. Specifically, a steroid compound having the partial structure of ring A and ring B of the steroid skeleton represented by Formula (1) is reacted with a catalytic amount of copper halide in the presence of oxygen to obtain a steroid compound having the partial structure of ring A and ring B of the steroid skeleton represented by Formula (2):

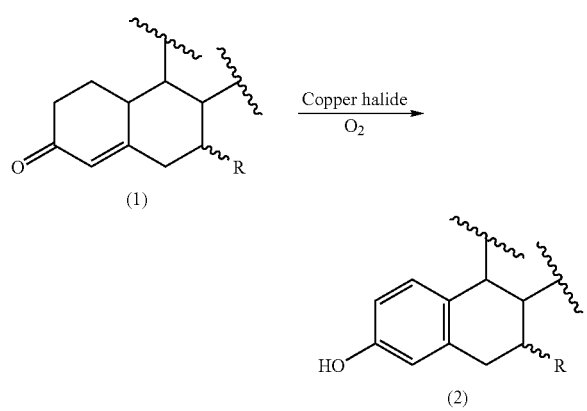

wherein R represents a hydrogen atom or $C_{1-6}$ alkyl group.

Examples of the copper halides usable in this step include copper (I) bromide, copper (II) bromide, copper (I) chloride, copper (II) chloride and the like. Among these, copper (II) bromide and copper (II) chloride are preferable, and copper (II) bromide is particularly preferable.

The copper halide can be used in a catalytic amount. The amount of copper halide is generally less than 1 mol, preferably 0.05 to 0.95 mol, and more preferably 0.2 to 0.8 mol per 1 mol of steroid compound having the partial structure of ring A and ring B of the steroid skeleton represented by Formula (1). In particular, when copper (II) bromide or copper (II) chloride is used as a copper halide, and 4-estrene-7a-methyl-3,17-dione is used as a steroid compound having the partial structure of ring A and ring B of the steroid skeleton represented by Formula (1), the amount of the copper (II) bromide or copper (II) chloride is generally 0.05 to 0.95 mol, and preferably 0.2 to 0.8 mol per 1 mol of 4-estrene-7a-methyl-3,17-dione. As described above, in the present invention, the amount of copper halide used can be remarkably reduced and therefore it is economical. Furthermore, the method of the present invention is environmentally friendly, since the amount of copper waste can be reduced.

There is no limitation to the solvents used in this step as long as they do not adversely affect the reaction. Examples thereof include acetonitrile, N,N-dimethyl formamide and like aprotic polar solvents; dimethoxyethane, tetrahydrofuran, dioxane and like ethers; ethyl acetate; acetic acid and the like. These solvents may be used singly or in combination. Among these, acetonitrile is preferable.

The steroid compound having a partial structure of ring A and ring B of its steroid skeleton represented by Formula (1) may be dissolved or suspended in a solvent. In terms of the reactivity, it is preferable that the steroid compound be used in a solution condition. The concentration of the steroid compound varies depending on the types of the steroid compounds and the solvent, but generally it falls within the range from about 0.05 mol/L to about 1.4 mol/L.

The reaction of the present invention may proceed using only by the oxygen dissolved and remained in the solvent of the reaction system. However, in industrial production, in order to accelerate the reaction and increase the yield of the objective product, it is preferable that an oxygen-containing gas be introduced or supplied to the reaction system. There is no limitation to the concentration of the oxygen of the oxygen-containing gas as far as it falls within a range from about 10 volume % to about 100 volume %. Examples of the oxygen-containing gases include oxygen, a gas obtained by diluting oxygen with inactive gas, air and the like.

Specifically, the reaction can be conducted by supplying (introducing) an oxygen-containing gas to a mixture of a steroid compound having the partial structure of ring A and ring B of the steroid skeleton represented by Formula (1), a catalytic amount of copper halide, and a solvent. More specifically, the reaction may be conducted under an oxygen-containing gas atmosphere, or while supplying an oxygen-containing gas (bubbling, etc.) in the reaction system. Conducting reaction under an oxygen-containing gas atmosphere is particularly preferable.

It is preferable that the oxygen-containing gas be free from water. Therefore, the gas is preferably used after drying over calcium chloride, potassium hydroxide, sodium hydroxide, concentrated sulfuric acid or like desiccating agent.

The feed rate and feed time of the oxygen-containing gas vary depending on the amount of the steroid compound having the partial structure of ring A and ring B of the steroid skeleton represented by Formula (1), which is a starting material, the type and amount of the solvent, reaction temperature, etc. For example, when 4-estrene-7a-methyl-3,17-dione is used as a starting material, the feed rate of the oxygen-containing gas is generally 1 to 10,000 mL/min/L, preferably 10 to 8,000 mL/min/L, and more preferably 10 to 5,000 mL/min/L. The feed time varies depending on the feed rate, and the total feed time, intermittently or continuously, is generally 0.01 to 8 hours, preferably 0.01 to 4 hours, and more preferably 0.05 to 2 hours.

The reaction temperature is generally 0° C. to 120° C., preferably 20° C. to 80° C., and more preferably 30° C. to 60° C. The reaction time is generally 0.1 to 48 hours, preferably 0.5 to 36 hours, and more preferably 0.5 to 6 hours.

The reaction proceeds favorably under such conditions. In other words, prior art techniques require an excessive amount of copper halide relative to the amount of a starting material; however, by actively supplying oxygen into the reaction system as defined in the production method of the present invention, a desired aromatized compound can be obtained at a high yield using a less catalytic amount of copper halide.

The compound obtained by the present production method can generally be isolated and refined using column chromatography, recrystallization and like known isolation and refining means. In particular, in the present invention, an objective compound can be selectively produced at a high yield in the reaction system, and therefore isolation and refinement can be conducted by simple recrystallization. Accordingly, the production process of the present invention is remarkably industrially advantageous.

EFFECT OF THE INVENTION

The present invention provides a production method by which ring A of a steroid skeleton can be easily and effectively aromatized by oxidation in a safe, economical, and environmentally friendly manner, without using any special apparatus. This allows the obtainment of 7α-methylestrone in an industrially effective manner by using 4-estrene-7a-methyl-3,17-dione as a starting material.

BEST MODE FOR CARRYING OUT THE INVENTION

The production method of the present invention is explained in detail below with reference to Examples and Comparative Examples. However, the production method of the present invention is not limited to these Examples.

Example 1

Synthesis of 7α-Methylestrone

An 80.0 g (0.280 mol) quantity of 4-estrene-7a-methyl-3,17-dione was suspended in acetonitrile (400 mL) into which oxygen had been blown (1,000 mL/min) in advance for one minute, 25.0 g (0.112 mol) of copper (II) bromide was added thereto, and then the resulting mixture was agitated for 1.5 hours under an oxygen atmosphere in an oil bath at 40° C. The solvent of the reaction solution was removed under reduced pressure, and the residue was extracted using chloroform. The thus-obtained extract was washed with water, dried over anhydrous magnesium sulfate, and subjected to filtration. The solvent of the extract was then removed under reduced pressure. The obtained precipitate was recrystallized from acetonitrile, giving 66.8 g (yield 84%) of 7α-methylestrone.

Melting point: 236° C. to 237° C.

MS (EI): 284 (M$^+$).

$^1$H-NMR (DMSO-d$_6$) d: 0.82 (3H, d, J=7.9 Hz), 0.83 (3H, s), 2.98 (1H, dd, J=16.7, 5.8 Hz), 6.44 (1H, d, J=2.5 Hz), 6.52 (1H, d, J=8.4, 2.5 Hz), 7.07 (1H, d, J=8.4 Hz) ppm.

Example 2

Synthesis of 7α-Methylestrone

A 50.0 g (0.175 mol) quantity of 4-estrene-7a-methyl-3,17-dione was suspended in acetonitrile (500 mL), and 23.5 g (0.105 mol) of copper (II) bromide was added thereto. Thereafter, air was blown (3,000 mL/min) into the reaction mixture every hour for one minute in an oil bath at 40° C. while agitating for 9 hours. Additional agitation was conducted at the same temperature for 13 hours, and then air was blown (3,000 mL/min) into the reaction mixture every hour for one minute while agitating for 4 hours. The solvent of the reaction solution was removed under reduced pressure, and the residue was extracted using chloroform. The thus-obtained extract was washed with water, dried over anhydrous magnesium sulfate, and subjected to filtration. The solvent of the extract was then removed under reduced pressure. The obtained precipitate was subjected to recrystallization from methanol, giving 36.5 g (yield at 73%) of 7a-methylestrone.

Example 3

Synthesis of 7α-Methylestrone

A 5.0 g (17.5 mmol) quantity of 4-estrene-7a-methyl-3,17-dione was dissolved in acetonitrile (100 mL), and 0.78 g (3.50 mmol) of copper (II) bromide was added thereto while agitating for 6 hours under an oxygen atmosphere in an oil bath at 40° C. The solvent of the reaction solution was removed under reduced pressure, and the residue was extracted using chloroform. The thus-obtained extract was washed with water, dried over anhydrous magnesium sulfate, and subjected to filtration. The solvent of the extract was then removed under reduced pressure. The obtained precipitate was subjected to recrystallization from methanol, giving 3.59 g (yield 72%) of 7α-methylestrone.

Example 4

Synthesis of 7α-Methylestrone

A 5.0 g (17.5 mmol) quantity of 4-estrene-7a-methyl-3,17-dione was dissolved in acetonitrile (100 mmol), and 1.88 g (14.0 mmol) of copper (II) chloride was added thereto. Thereafter, air was blown (1,000 mL/min) into the reaction mixture every hour for one minute in an oil bath at 40° C. while agitating for 5 hours. The solvent of the reaction solution was removed under reduced pressure, and the residue was extracted using chloroform. The thus-obtained extract was washed with water, dried over anhydrous magnesium sulfate, and subjected to filtration. The solvent of the extract was then removed under reduced pressure. The obtained precipitate was subjected to recrystallization from methanol, giving 2.58 g (yield 52%) of 7α-methylestrone.

Example 5

Synthesis of 7α-Methylestrone

A 5.0 g (17.5 mmol) quantity of 4-estrene-7a-methyl-3,17-dione was dissolved in acetonitrile (100 mmol), and 3.13 g (14.0 mmol) of copper (II) bromide was added thereto. Subsequently, air was blown (1,000 mL/min) onto the surface of the reaction mixture in an oil bath at 40° C. every hour for one minute while agitating for 3 hours. The solvent of the reaction solution was removed under reduced pressure, and the residue was extracted using chloroform. The thus-obtained extract was washed with water, dried over anhydrous magnesium sulfate, and subjected to filtration. The solvent of the extract was then removed under reduced pressure. The obtained precipitate was subjected to recrystallization from methanol, giving 4.05 g (yield 81%) of α-methylestrone.

Comparative Example 1

Necessity of Oxygen

A 5.0 g (17.5 mmol) quantity of 4-estrene-7a-methyl-3,17-dione was dissolved in acetonitrile (100 mL), and 3.13 g (14.0 mmol) of copper (II) bromide was added thereto while agitating for 18 hours under a nitrogen atmosphere in an oil bath at 40° C. The solvent of the reaction solution was removed under reduced pressure, and the residue was extracted using chloroform, washed with water, dried over anhydrous magnesium sulfate, and subjected to filtration. The solvent of the extract was then removed under reduced pressure, giving a mixture of 4-estrene-7a-methyl-3,17-dione and 7α-methyl-estrone with a ratio of 58:42.

Comparative Example 2

Necessity of Copper (II) Bromide or Copper (II) Chloride

A 5.0 g (17.5 mmol) quantity of 4-estrene-7a-methyl-3,17-dione was dissolved in acetonitrile (100 mL) into which oxygen had been blown (1,000 mL/min) for one minute in advance. Subsequently, agitation was conducted in an oil bath at 40° C. under an oxygen atmosphere for 6 hours. The solvent of the reaction solution was removed under reduced pressure, and the residue was extracted using chloroform, washed with water, dried over anhydrous magnesium sulfate, and subjected to filtration. The solvent of the extract was then removed under reduced pressure, recovering 4-estrene-7a-methyl-3,17-dione, which is a starting material.

The invention claimed is:

1. A process for producing a steroid compound having a partial structure of ring A and ring B of a steroid skeleton represented by Formula (2):

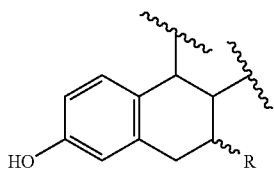

(2)

wherein R represents a hydrogen atom or $C_{1-6}$ alkyl group, comprising the step of reacting a steroid compound having a partial structure of ring A and ring B of a steroid skeleton represented by Formula (1):

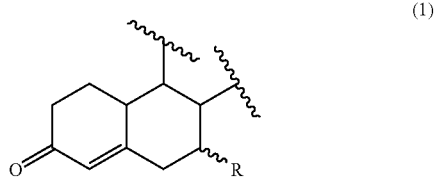

(1)

wherein R is the same as above;
with a catalytic amount of copper halide in the presence of oxygen.

2. A production process according to claim 1, wherein 0.05 to 0.95 mol of copper halide is used per 1 mol of a steroid compound having the partial structure of ring A and ring B of the steroid skeleton represented by Formula (1).

3. A production process according to claim 1, wherein the copper halide is copper (II) bromide or copper (II) chloride.

4. A production process according to claim 1, wherein the reaction is conducted while supplying an oxygen-containing gas to a mixture of a steroid compound having the partial structure of ring A and ring B of the steroid skeleton represented by Formula (1), a catalytic amount of copper halide, and a solvent.

5. A production process according to claim 1, wherein R in Formula (1) and Formula (2) is methyl group.

6. A production process according to claim 1, wherein the steroid compound having the partial structure of ring A and ring B of the steroid skeleton represented by Formula (1) is 4-estrene-7a-methyl-3,17-dione and the steroid compound having the partial structure of ring A and ring B of the steroid skeleton represented by Formula (2) is 7α-methylestrone.

* * * * *